US008150707B2

(12) United States Patent
Hayet et al.

(10) Patent No.: US 8,150,707 B2
(45) Date of Patent: Apr. 3, 2012

(54) METHOD AND APPARATUS FOR ASSISTING BEHAVIOURAL CHANGE

(76) Inventors: Christine Marie Hayet, Sharnbrook (GB); Robert Hurling, Sharnbrook (GB); Brian Patrick Newby, Wirral (GB); Shail Patel, Sharnbrook (GB)

( * ) Notice: Subject to any disclaimer, the term of this patent is extended or adjusted under 35 U.S.C. 154(b) by 489 days.

(21) Appl. No.: 12/097,512

(22) PCT Filed: Dec. 16, 2005

(86) PCT No.: PCT/US2005/045969
§ 371 (c)(1),
(2), (4) Date: Mar. 25, 2009

(87) PCT Pub. No.: WO2007/070062
PCT Pub. Date: Jun. 21, 2007

(65) Prior Publication Data
US 2010/0030857 A1    Feb. 4, 2010

(51) Int. Cl.
*G06Q 50/00* (2012.01)
(52) U.S. Cl. .................................. 705/2; 705/3
(58) Field of Classification Search .................. 434/236; 600/300; 705/2, 3
See application file for complete search history.

(56) References Cited

U.S. PATENT DOCUMENTS

| 5,879,163 | A | 3/1999 | Brown et al. |
| 2002/0070954 | A1 | 6/2002 | Lang |
| 2003/0027116 | A1 | 2/2003 | O'Donnell |
| 2003/0036042 | A1* | 2/2003 | Hill ............................... 434/236 |
| 2003/0186202 | A1* | 10/2003 | Isenberg ........................ 434/236 |
| 2005/0113650 | A1* | 5/2005 | Pacione et al. ................ 600/300 |
| 2005/0182773 | A1 | 8/2005 | Feinsmith |
| 2005/0240434 | A1* | 10/2005 | Wooten et al. ..................... 705/2 |
| 2006/0019225 | A1* | 1/2006 | Orman ........................... 434/236 |

FOREIGN PATENT DOCUMENTS

| EP | 1548682 A2 | 6/2005 |
| JP | 2002-263107 A | 9/2002 |
| JP | 2005-181241 A | 7/2005 |
| WO | 03/009260 A1 | 1/2003 |
| WO | 2005/091195 A1 | 9/2005 |

OTHER PUBLICATIONS

International Search Report received for PCT Patent Application No. PCT/US2005/45969, mailed on Aug. 18, 2006, 3 pages.
Office Action received for Japanese Patent Application No. 2008-545556, mailed on Jul. 26, 2011, 5 pages (3 pages of English Translation and 2 pages of Office Action).

* cited by examiner

*Primary Examiner* — Le Luu
(74) *Attorney, Agent, or Firm* — Morrison & Foerster LLP

(57) ABSTRACT

A method and apparatus for assisting a user to formulate, apply and adhere to a changed behavior program. The user's commitment is established by presenting a number of potential barriers to implementing a desired behavioral change; asking a user to select one or more potential barriers; presenting a selected number of possible solutions to the barriers, receiving user input selecting at least one solution; and prompting the user to enter a commitment to one or more actions intended to assist the behavioral change. Maintenance of an exercise regime is assisted by displaying a selection of options for activities to be included in the exercise regime; allowing a user to select activities; displaying a schedule of planned exercise activities; and sending an electronic alert message to the user in advance of the scheduled activity.

20 Claims, 11 Drawing Sheets

Fig. 4.

get·active!
a new approach to exercise motivation

110

Barrier:
I don't want to get all sweaty

Several people have found the following solutions have helped them overcome this barrier:

| Select | Solution | Rating |
|---|---|---|
| ■Submit Query | Try an alternative perspective "Healthy Sweat is my friend, and I only get to see her when I exercise hard." | ★★★★☆ |
| ■Submit Query | People who go to the gym regularly get used to looking a bit different afterwards, and eventually consider these side effects as a 'symbol' demonstrating to others that they've been exercising. Try thinking of them as something positive, and perhaps even tell others that you've been exercising. | ★★★★☆ |
| ■Submit Query | Think of sweat as a sign of your success. | ★★★★☆ |

If one of these is relevant to you then click 'Select' to proceed and the solution will be automatically entered on your Plan, so that you can use it later to think about how you'll overcome your key barrier to exercise.

Remember that sometimes the solution might seem fairly simple or obvious but it's the willingness to commit to doing something about it that really counts.

If you don't wish one of these solutions to be entered on your plan, navigate back to the barrier menu.

You can also select a second barrier to focus on.

■ Desubmit Query...

Sidebar (left):
- Home
- My Plan
- Talk to Dora...
- Pick your Own
- Commitment Page
- Benefits Page
- Schedule
- Options
- Other Activities
- Exercise Charts
- Motivational Tips
- Buddy Page
- You can work it out!
- Suggest Solutions
- Message Board
- Contact Us
- Log Out

Plan Summary (right):

my barriers and solutions
Barrier:
It's too much hassle to do my make-up & hair afterwards
Solution:
Cooling down before starting to change also helps. Regular exercisers develop a different hair / make-up routine for after exercising that's simpler - try asking some of your friends or fellow exercisers what they do.

my commitment my benefits
Exercise takes my mind off other things for a while
Regular exercise would help me have a more positive outlook on life
Exercise improves my mood my schedule
Fri : Evening : Swimming my preferences
Buddy Opt In: No
Motivational Messages: No
Benefit Messages: No
Gym Reminders: Yes-SMS
kit Reminders: No

Fig.5.

get·active!
a new approach to exercise motivation

| Home |
| My Plan |
| Talk to Dora... |
| Pick your Own |
| Commitment Page |
| Benefits Page |
| Schedule |
| Options |
| Other Activities |
| Exercise Charts |
| Motivational Tips |
| Buddy Page |
| You can work it out! |
| Suggest Solutions |
| Message Board |
| ☒ Contact Us |
| ☒ Log Out |

Barrier:
I don't want to get all sweaty                                         114

Several people have found the following solutions have helped them overcome this barrier:   116

| Select | Solution | Rating |
|---|---|---|
| ■Submit Query | Activity does make you sweat. If you're enjoying yourself at your activity you tend not to notice and everyone else is sweaty too. The great part is the rewarding shower afterwards. | ★★★★☆ |
| ■Submit Query | Face glowing, muscles pumped, hair tousled, adrenaline flowing-remind you of any other occasion!? | ★★★☆☆ |
| ■Submit Query | Try allocating more time to cool down and get changed after exercising, perhaps you could eat your lunch or read a book to make the time more useful. | ★★★☆☆ |

12

If one of these is relevant to you then click 'Select' to proceed and the solution will be automatically entered on your Plan, so that you can use it later to think about how you'll overcome your key barrier to exercise.

Remember that sometimes the solution might seem fairly simple or obvious but it's the willingness to commit to doing something about it that really counts.

If you don't wish one of these solutions to be entered on your plan, navigate back to the barrier menu.

You can also select a second barrier to focus on.

■ Desubmit Query...

115

Plan Summary my barriers and solutions
Barrier:
It's too much hassle to do my make-up & hair afterwards
Solution:
Cooling down before starting to change also helps. Regular exercisers develop a different hair / make-up routine for after exercising that's simpler - try asking some of your friends or fellow exercisers what they do.  117  118 my commitment
Exercise takes my mind off other things for a while my benefits
Regular exercise would help me have a more positive outlook on life
Exercise improves my mood my schedule
Fri : Evening : Swimming my preferences
Buddy Opt In: No
Motivational Messages: No
Benefit Messages: No
Gym Reminders: Yes-SMS
kit Reminders: No

Fig.7.

get·active!
*a new approach to exercise motivation*

130

| Navigation | |
|---|---|
| Home | |
| My Plan | |
| Talk to Dora... | |
| Pick your Own | |
| Commitment Page | |
| Benefits Page | |
| Schedule | |
| Options | |
| Other Activities | |
| Exercise Charts | |
| Motivational Tips | |
| Buddy Page | |
| You can work it out! | |
| Suggest Solutions | |
| Message Board | |
| Contact Us | |
| Log Out | |

Here are the solutions that you selected.

Barrier:
It's too much hassle to do my make-up & hair afterwards
Solution:
Cooling down before starting to change also helps. Regular exercisers develop a different hair / make-up routine for after exercising that's simpler - try asking some of your friends or fellow exercisers what they do.

Barrier:
I don't want to get all sweaty
Solution:
Try allocating more time to cool down and get changed after exercising, perhaps you could eat your lunch or read a book to make the time more useful.

Review these solutions and then write in the box, in your own words, how YOU will overcome the barriers that have been preventing you from exercising as much as you want.

Be as specific and detailed as you can - it really will help !

```
I will swim twice a week and go to the gym once a week.
```
131

▶Submit Query

---

Plan Summary

*my barriers and solutions*

Barrier:
It's too much hassle to do my make-up & hair afterwards
Solution:
Cooling down before starting to change also helps. Regular exercisers develop a different hair / make-up routine for after exercising that's simpler - try asking some of your friends or fellow exercisers what they do.

Barrier:
I don't want to get all sweaty
Solution:
Try allocating more time to cool down and get changed after exercising, perhaps you could eat your lunch or read a book to make the time more useful.

*my commitment*

I will swim twice a week.

*my benefits*

Exercise takes my mind off other things for a while
Regular exercise would help me have a more positive outlook on life
Exercise improves my mood

*my schedule*

Tue : Evening : Swimming
Fri : Evening : Swimming
Sun : Morning : Gym

Fig. 8.

get·active!
a new approach to exercise motivation

140

| Home |
|---|
| My Plan |
| Talk to Dora... |
| Pick your Own |
| Commitment Page |
| Benefits Page |
| Schedule |
| Options |
| Other Activities |
| Exercise Charts |
| Motivational Tips |
| Buddy Page |
| You can work it out! |
| Suggest Solutions |
| Message Board |

| Contact Us |
| Log Out |

Look through the list of benefits below and select up to three that most motivate you to go to the gym.

▪Submit Query

- ☑ I would look and feel better if I exercise more
- ☑ Exercise will help me with weight loss
- ☐ I will have more energy
- ☐ Exercise improves my mood
- ☐ Exercise will help me maintain a healthy weight
- ☑ I will reduce the risk of heart disease and many other health problems
- ☐ Exercise takes my mind off other things for a while
- ☐ Exercise will improve the quality of my life
- ☐ I will have increased stamina
- ☐ I will be more flexible
- ☐ Exercising increases my feeling of self-respect
- ☐ Regular exercise would help me have a more positive outlook on life
- ☐ Exercise will increase my self-esteem
- ☐ Exercising now will help me have a fit and active retirement one day
- ☐ Exercise provides valuable 'me-time' when I devote a whole hour to just my needs
- ☐ Will increase my confidence
- ☐ I can make friends whilst exercising  ← 142

↖ 144

Plan Summary my barriers and solutions

Barrier:
It's too much hassle to do my make-up & hair afterwards
Solution:
Cooling down before starting to change also helps. Regular exercisers develop a different hair / make-up routine for after exercising that's simpler - try asking some of your friends or fellow exercisers what they do.

Barrier:
I don't want to get all sweaty
Solution:
Try allocating more time to cool down and get changed after exercising, perhaps you could eat your lunch or read a book to make the time more useful.

my commitment
I will swim twice a week and go to the gym once a week.

my benefits
Exercise takes my mind off other things for a while
Regular exercise would help me have a more positive outlook on life
Exercise improves my mood my schedule
Tue : Evening : Swimming
Fri : Evening : Swimming

Fig.9.

get·active!
*a new approach to exercise motivation*

150

It has been shown that planning when and how you will exercise in advance makes it more likely that it will happen. Be realistic about what you think you can achieve in the week and build up gradually.

Use the table to select what you want to do and when you will do it. Click on a square to cycle through exercise activities and then select the starting time using the drop down list. You'll only be able to edit squares later than the current time for this week. To save your schedule click 'Submit'.

Currently Editing: 151
This Week

Schedule Key:
- Gym
- Running
- Swimming
- Other  155

Port Sunlight Gym
Opening Times:
Wed/Fri 7.30-9.30am
Mon-Fri 12-2pm
Mon-Thu 4-7.30pm
Fri 4-6pm

|  | Mon | Tue | Wed | Thu | Fri | Sat | Sun |
|---|---|---|---|---|---|---|---|
| Morning |  |  |  |  |  |  | 153 / 09:00:00 154 |
| Lunchtime |  |  |  |  |  |  |  |
| Afternoon |  |  |  |  | 17:00:00 |  |  |
| Evening | 152 / 17:00:00 154 |  |  |  |  |  |  |

■Submit Query  156
Edit Submit Query>>  157

- Home
- My Plan
  - Talk to Dora...
  - Pick your Own
  - Commitment Page
  - Benefits Page
  - Schedule
  - Options
- Other Activities
  - Exercise Charts
  - Motivational Tips
  - Buddy Page
  - You can work it out!
  - Suggest Solutions
  - Message Board
- ☒ Contact Us
- ☒ Log Out

Fig. 10.

| Home |
| My Plan |
| Talk to Dora... |
| Pick your Own |
| Commitment Page |
| Benefits Page |
| Schedule |
| Options |
| Other Activities |
| Exercise Charts |
| Motivational Tips |
| Buddy Page |
| You can work it out! |
| Suggest Solutions |
| Message Board |

☑ Contact Us
☒ Log Out get·active!
a new approach to exercise motivation

160

Below are a range of options that will help you achieve your desired exercise level. Move your mouse over each to find what they're about. Click on those you'd like to receive.

Try them out - you can come back in and turn them off whenever you want!

161 ☐ Opt-in to the Buddy System
162 ☑ Exercise Session Reminders    How: [SMS ▼]    Minutes before: [30 ▼] — 167
163 ☑ Kit Reminders    How: [SMS ▼]    Evening Before: [20:00 ▼]
164 ☐ Benefit Reminders
165 ☑ Motivational Reminders
                                            166

To receive text reminders, enter your mobile phone number: [0770 000 0000] — 168

[■Submit Query] — 169

Plan Summary my barriers and solutions
Barrier:
It's too much hassle to do my make-up & hair afterwards
Solution:
Cooling down before starting to change also helps. Regular exercisers develop a different hair / make-up routine for after exercising that's simpler - try asking some of your friends or fellow exercisers what they do.
Barrier:
I don't want to get all sweaty
Solution:
Try allocating more time to cool down and get changed after exercising, perhaps you could eat your lunch or read a book to make the time more useful.

my commitment
I will swim twice a week and go to the gym once a week.

my benefits
Exercise takes my mind off other things for a while
Regular exercise would help me have a more positive outlook on life
Exercise improves my mood my schedule
Tue : Evening : Swimming
Fri : Evening : Swimming

METHOD AND APPARATUS FOR ASSISTING BEHAVIOURAL CHANGE

The present invention relates to methods and apparatus for assisting a user to make behavioural changes, and in particular for assisting the user to formulate, apply and adhere to a behaviour program, such as an exercise regime.

Many people find it difficult to modify their behaviour patterns to a desired mode of behaviour. Furthermore, many people find it even more difficult to maintain such a mode of behaviour over an extended period of time. For example, many people now recognise that a more active lifestyle involving regular sessions of exercise is a desirable objective to obtain long term health benefits and a sense of general well-being. Unfortunately, many people find it difficult to know where to start on such a suitable exercise program, difficult to overcome perceived obstacles in starting such a program, and difficult to maintain such a program in the face of conflicting lifestyle pressures.

For many people, the only realistic way to achieve the goal of a long term change in exercise regime is to use the services of a professional personal trainer or instructor who will plan a suitable program and consistently provide personal support, motivation and encouragement to help the person maintain and adhere to the appropriate desired level of activity. However, this is an expensive solution that is not readily available to many people, not least on the grounds of cost.

US 2003/0027116 describes a method for assisting a person in changing a behaviour such as smoking, by having the person assess quantitatively the degree of readiness to change and the difficulty of changing a behaviour; by having the person list benefits and obstacles involved in changing the behaviour and by devising a strategy for changing the behaviour that includes positive reinforcement and self-efficacy.

WO 03/009260 describes a method for improving patient compliance with a treatment regimen where the patient accesses a web page, selects a virtual guide, inputs data and receives customised e-mail messages in the style and tone of the virtual guide intended to motivate and educate the patient.

The present invention seeks to provide an automated system for providing a user with initial and continuing practical support in the formulation and continuing application of a behavioural change such as adherence to an exercise program.

It is an object of the present invention to provide an automated system for assisting in the creation and maintenance of an encouraging, motivational environment for a user to assist the user to adhere to a modified behaviour program.

According to one aspect, the present invention provides an apparatus for assisting behavioural change in an individual, comprising:
  means for receiving user input indicating one or more potential barriers to implementing a desired behavioural change;
  means for presenting to the user a selected number of possible solutions to the barriers, the possible solutions being selected from a database of solutions according to a strength of association with or mapping from the barriers identified in said user input;
  means for receiving user input selecting at least one said solution; and
  means for prompting the user to enter a commitment to one or more actions intended to assist the behavioural change.

According to another aspect, the present invention provides a method of assisting behavioural change in an individual, which method comprises:

(a) identifying in the individual a barrier to implementing the desired behavioural change, said barrier being selected from a predetermined list;
(b) selecting one or more solutions to the barrier using a system comprising a mapping between barriers and solutions, the selected one or more solutions having the highest strength of association with the barrier identified in step (a);
(c) presenting the one or more solutions to the individual;
(d) verifying the individual's acceptance of the one or more solutions, with steps (b) and (c) being repeated until the individual accepts at least one solution; and
(e) prompting the individual to enter a commitment to one or more actions intended to assist the desired behavioural change.

According to another aspect, the present invention provides an apparatus for assisting in maintenance of an exercise regime in an individual, comprising:
  means for displaying to the user a selection of options for activities to be included in the exercise regime;
  means for receiving a user selection of activities and scheduled times for the activities;
  schedule display means for displaying a schedule of planned exercise activities; and
  alert means for sending an electronic alert message to the user in advance of a scheduled activity.

Embodiments of the present invention will now be described by way of example and with reference to the accompanying drawings in which:

FIG. 4 is a web page, transmitted by the server of FIG. 1, listing solutions to a selected barrier of FIG. 3 from which the user may make a selection;

FIG. 5 is a web page, transmitted by the server of FIG. 1, listing further solutions to the selected barrier from which the user may make a selection;

FIG. 7 is a web page, transmitted by the server of FIG. 1, summarising user selections of barriers and respective solutions;

FIG. 8 is a web page, transmitted by the server of FIG. 1, listing possible benefits of a behaviour change from which the user may make a selection;

FIG. 9 is a web page, transmitted by the server of FIG. 1, by which the user may complete a schedule of planned activities;

FIG. 10 is a web page, transmitted by the server of FIG. 1, listing a number of possible support options from which the user may make a selection.

Figure 1:
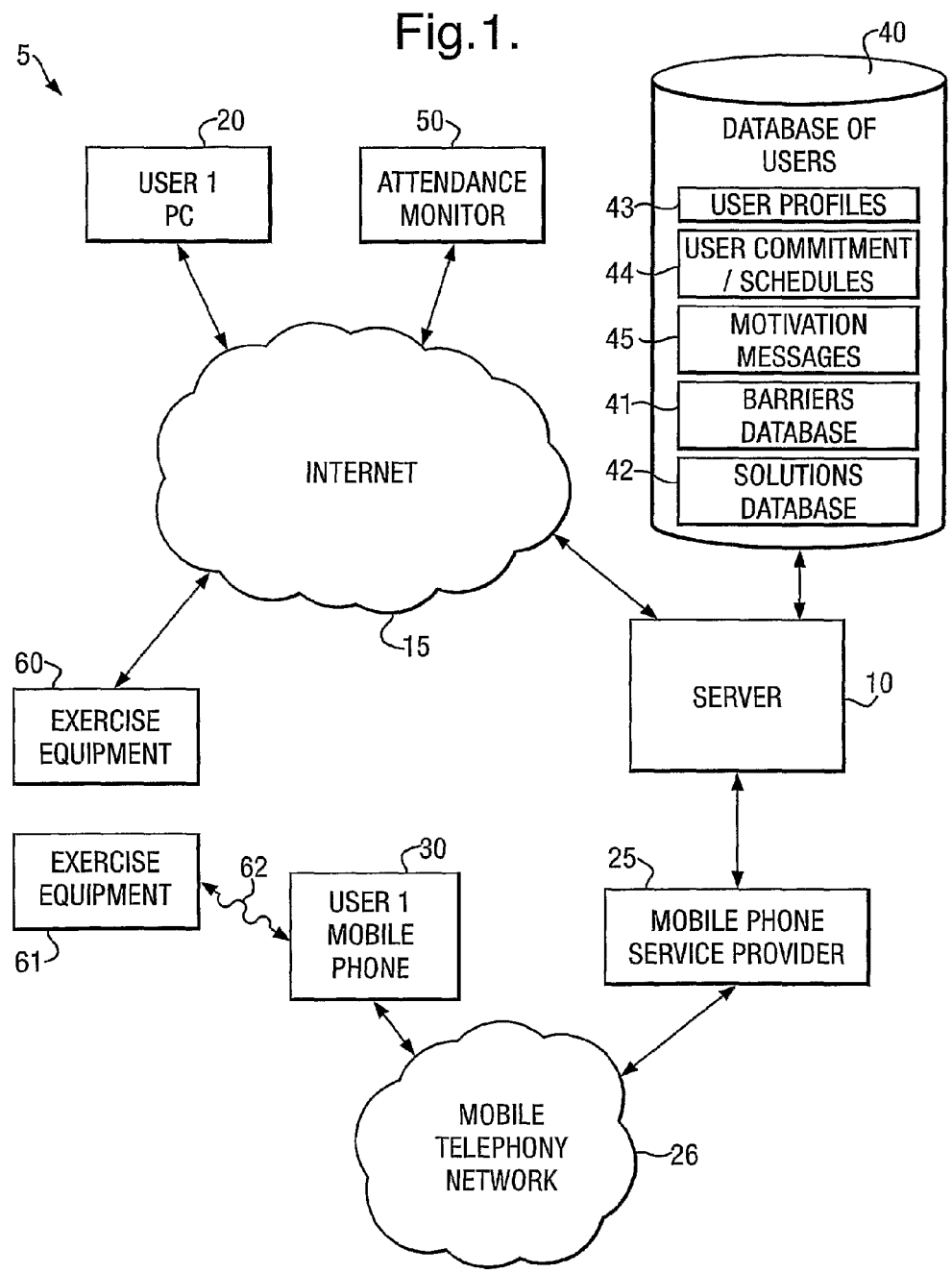
FIG. 1 shows a schematic diagram of a configuration of electronic data processing and communication media for implementing a user behavioural change motivation system.

In one aspect, the present invention recognises that for many people, the ability to adhere to a behaviour change such as an exercise program may be strongly influenced by, for example, the involvement of one or more third parties in the commitment either for supervision, monitoring, motivation, reminding or other interaction. One aspect of the invention facilitates such involvement in an automated or semi-automated manner using electronic data processing and communication media.

A preferred configuration of electronic data processing and communication media to implement a user motivation system 5 is described in connection with FIG. 1. A server 10 provides overall control of the functions provided the user motivation system 5. The server 10 provides for remote access by a plurality of users via at least one user computer system 20 using a suitable wired or wireless network 15 such as the internet.

The server 10 may provide a plurality of user interface web pages for input and output of data to the user as will be described below. The server 10 may also provide for generation of automated e-mails to be delivered by the network 15, as will be described below. The server 10 also may provide for generation of automated text messages to be delivered by way of a mobile telephone service provider server 25 and associated wireless telephony network 26 to a user's mobile telephone 30, as will be described in detail below. The server 10 maintains a database 40 of user and system information suitable for providing the user motivation service, as will be described in detail below.

The user motivation system may also encompass a plurality of feedback systems for acquiring and delivering data relating to the progress of users of the system, such as attendance monitoring systems 50 for gathering and transmitting data relating to users' attendance at predetermined exercise locations and exercise equipment 60, 61 for gathering and transmitting data relating to users' performance at predetermined exercise locations.

Figure 2:
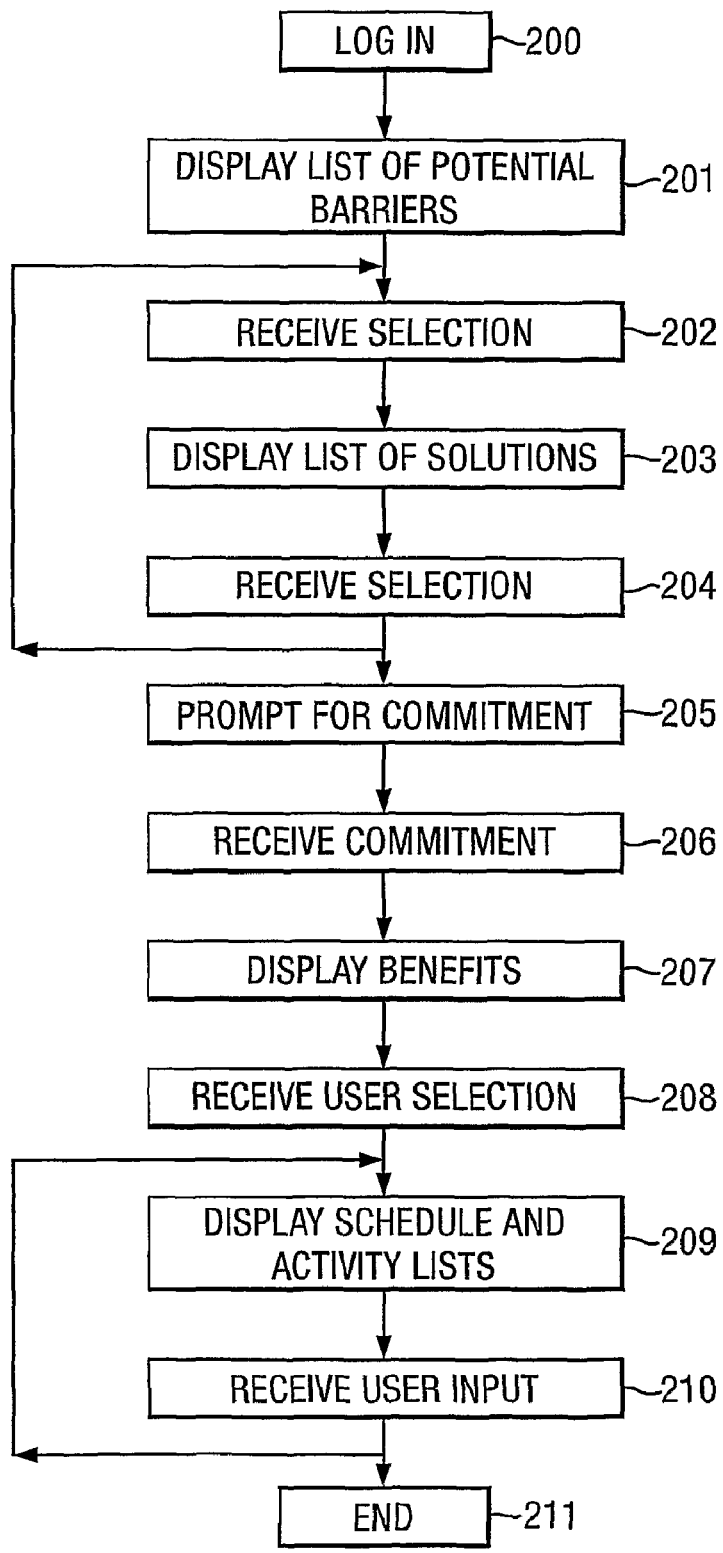
FIG. 2 is a flow chart of initial operations carried out by the server of FIG. 1.

With reference to FIG. 2, a preferred initialisation of a user's exercise program will now be described.

Figure 3:
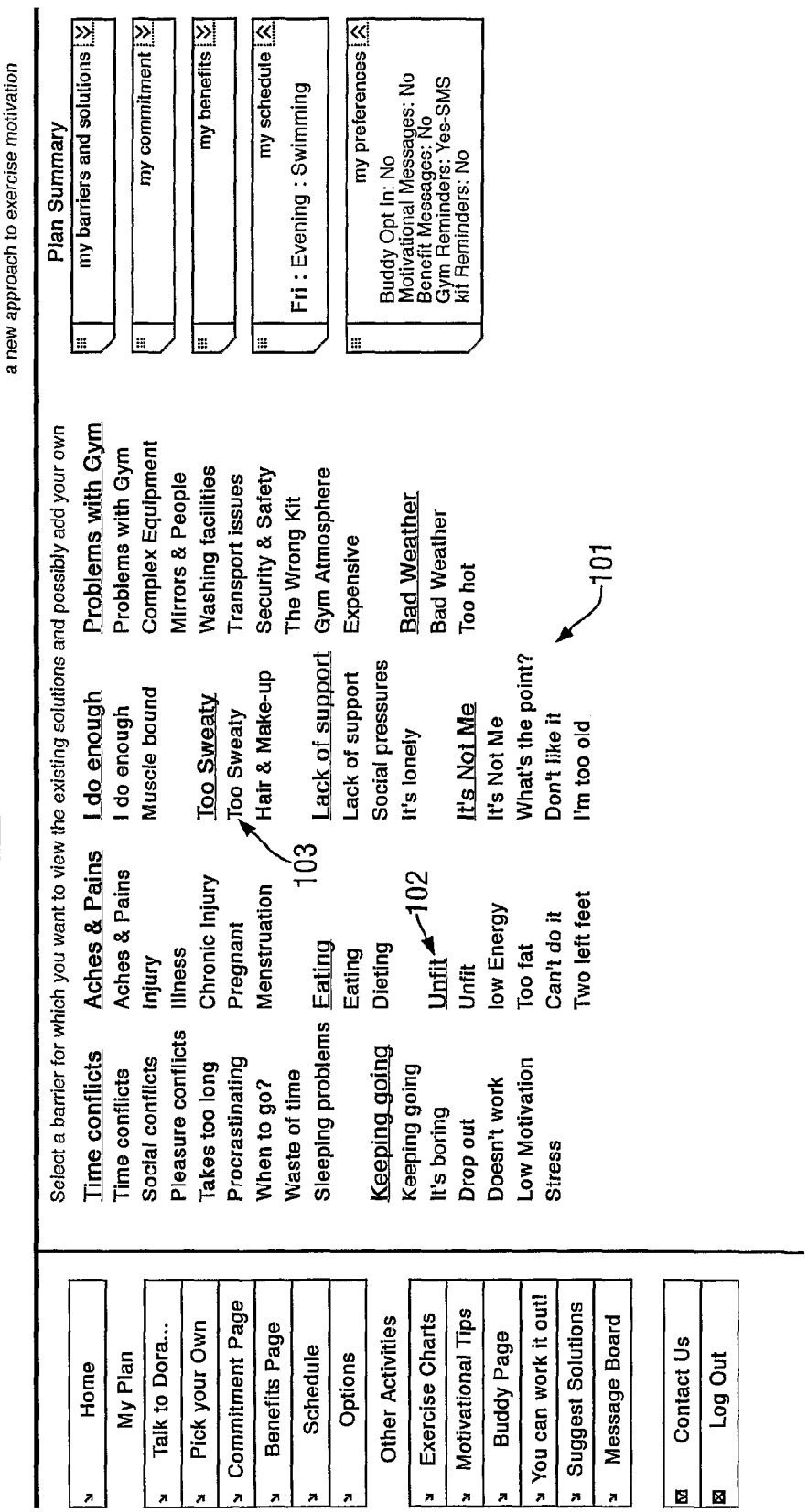
FIG. 3 is a web page, transmitted by the server of FIG. 1, listing barriers to behaviour change from which the user may make a selection.

A new user of the motivation system 5 logs in to the server 10 using remote computer system 20 via an appropriate communications channel 15 (step 200). After making appropriate selections to commence definition of a new plan, an appropriate web page 100 (FIG. 3) is displayed to the user (step 201). The 'barriers' web page 100 provides a list 101 of potential barriers to commencement and/or maintenance of an exercise plan from barriers database file 41. The barriers are defined according to those commonly found by many persons attempting to achieve more exercise. The list 101 is preferably formatted into various sections 102 each under an appropriate heading. The list may be ordered or prioritised (e.g. by highlighting etc) on a dynamic basis according to the most frequently selected by other users or according to the most frequently selected and successfully applied by other users of the system. The list may be ordered or prioritised according to those barriers usually most relevant to a predetermined user profile.

A user may select any of the barriers in the list 101, for example entry 103 corresponding to the perceived barrier that the user dislikes the fact that exercise makes one sweaty. The server 10 receives this selection (step 202) and transmits a new web page 110 (FIG. 4) which offers three 'solutions' 111, 112, 113 to consider for overcoming this particular barrier (step 203). The solutions are maintained in a solutions database file 42 linked to the barriers file 41 (FIG. 1). The user is also offered the opportunity to view one or more further web pages 115 (FIG. 5) which offers a further three 'solutions' 116, 117, 118 to consider for overcoming this particular barrier.

In a particularly preferred embodiment, the solutions are displayed to the user according to a 'strength of association' between the selected barrier and the displayed solution. The strength of association is preferably defined according to the popularity of a particular solution as determined by existing or previous users of the system. In other words, the strength of association is an indicator as to how many users have found a particular solution helpful in overcoming a barrier to change. More preferably, the strength of association is a dynamic feature that changes according to the most recently popular choices made by users. A 'star rating' 114 may be provided on each 'solutions' page 110, 115 as an indicator to the user of how popular or useful other users have found a given solution. The strength of association may be affected by feedback on a measure of efficacy for behavioural change, such that solutions that are reported to have a higher degree of success in achieving users' objectives have a higher strength of association. The 'measure of efficacy' may be determined subjectively (e.g. by user feedback) or objectively (e.g. by exercise results). The change in strength of association may be determined as a weighted balance of those solutions which are most popular and those which have the greatest impact on behavioural change. The strengths of association may be applied on a 'whole user group' basis (i.e. based on all users of the system) or on a sub-group of users having similar user profiles.

Figure 6:
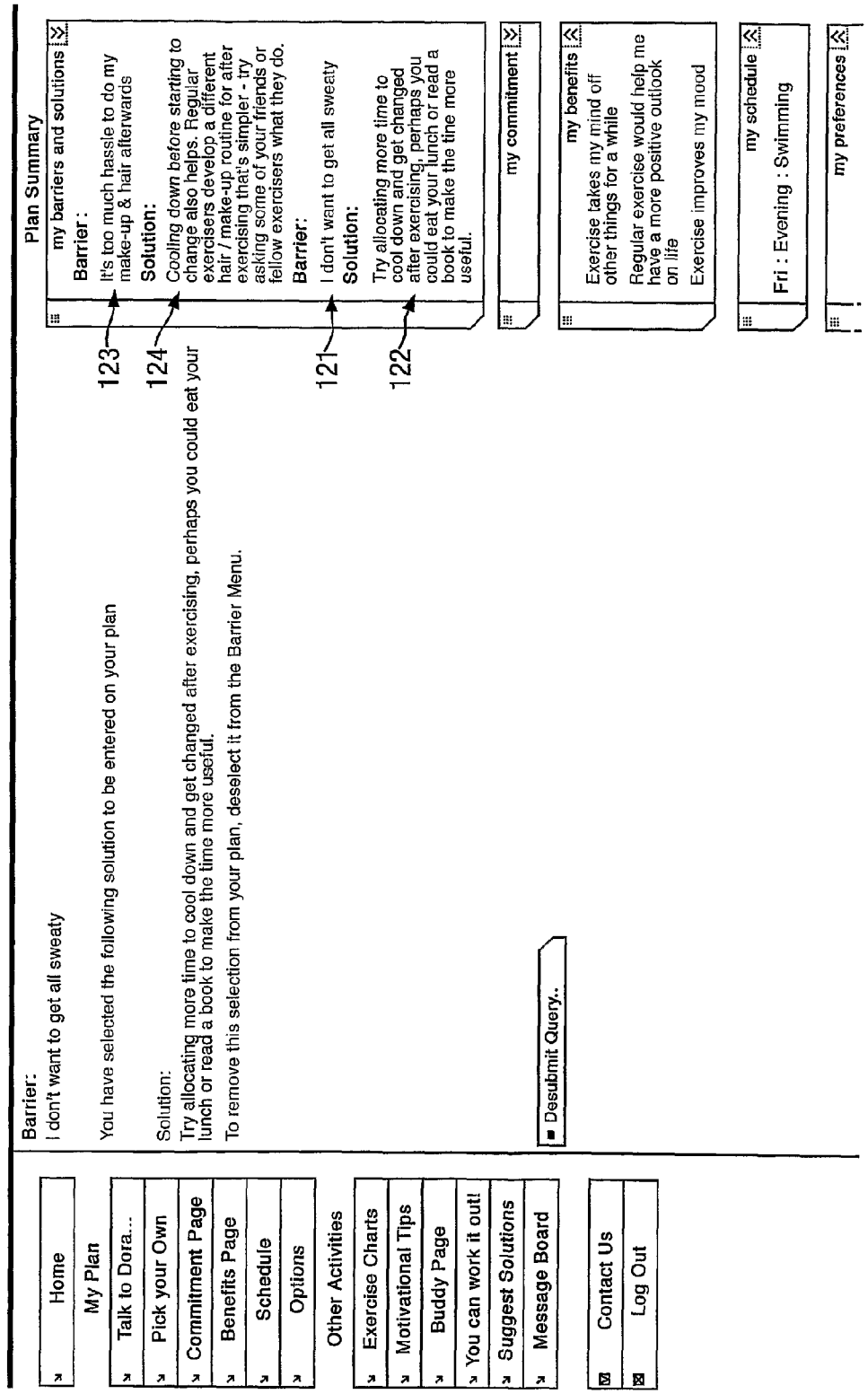
FIG. 6 is a web page, transmitted by the server of FIG. 1, summarising a user selection of barrier and solution.

The user selects one or more of the solutions from web page 110 or 115. When this selection is received by the server 10 (step 204), the server then transmits a confirmation web page 120, e.g. as shown in FIG. 6. The user may repeat steps 201 to 204 in order to view and possibly select more barriers and to view and possibly select more solutions. In the preferred embodiment, a user is invited to select only two barriers and only one solution to each barrier in order to maintain a degree of focus. These barriers 121 and solutions 122 are displayed to the right of the web page 120 (and subsequent web pages). In the example of FIG. 6, the user has also already selected another barrier 123 and solution 124, also displayed to the right of the web page 120. However, any number of barriers and solutions may be provided for.

Selected barriers and solutions are added to the user profile 43 (FIG. 1) stored in database 40.

The user is then prompted to make a commitment (step 205, FIG. 2). The server 10 transmits (step 205, FIG. 2) a 'commitment' web page 130 (FIG. 7). The commitment page 130 includes a dialogue box 131 into which the user may enter one or more exercise commitments to start their exercise program. The commitments might alternatively be provided as a list of optional possibilities based on the stored user profile 43. The stored user profile 43 may have been prepopulated with user information which could influence the list of offered exercise possibilities. For example, the user profile 43 may include medical, biometric or physical data indicative of what sorts of activities are appropriate for that user. The user profile 43 may also include a list of activities that are actually available to the specific user, e.g. based on the equipment and facilities available in an associated gym or health club or other facility local to the user.

The server 10 receives the user commitment (step 206) and updates a user commitment/schedule file 44 (FIG. 1). In another embodiment, not shown, the server 10 may be adapted to analyse the user commitment to determine how 'well-formed' it is. This preferably includes a test for how specific or deterministic the commitment is, particularly in terms of measurable achievement; for example the server may look for specific commitments to perform a certain type of activity (e.g. go to the gym or swimming pool) a certain number of times a week, rather than simply 'I intend to exercise more often'. The server may also look for specific time commitments (e.g. I shall go to the gym on Tuesdays and Thursdays for at least 30 minutes. The server 10 may enter a dialogue with the user to improve and refine the commitment to include more measurable objectives.

Once a commitment has been established and agreed, the server may then transmit a web page 140 (FIG. 8 and step 207) to prompt the user to review a list 141 of possible benefits of the exercise schedule. The list of benefits 141 may be sorted according to the most popular user choices. The most popular user choices may be determined on a dynamic basis constantly reflecting choices of current and past users of the system. The list 141 may be populated according to user profile data from the user profile file 43 and/or the user commitment/schedule file 44 to determine appropriate entries for inclusion in the list, or to determine inappropriate entries for exclusion from the list. The user selects a number of benefits from the list 141 by ticking appropriate check boxes 142 to the left of the web page and submits the completed web page to the server 10 (step 208).

The server then delivers (step 209) a 'scheduler' web page 150 (FIG. 9) to allow the user to schedule their selected activities on a week-by-week basis. Preferably, a list of available activities appears as a schedule key 151. Clicking an appropriate number of times in a box 152 (e.g. 'Tuesday evening' box) selects the activity by iterating through the options, e.g. swimming, running, cycling etc. Swimming has been selected in the illustration. Similarly, in box 153, the gym is selected for Sunday morning. Drop down boxes 154 may be used to select an appropriate time. Preferably, the drop down boxes 154 are controlled to only offer possible opening times of the selected required resource, e.g. gym opening times as displayed at 155, where applicable. The user selections are submitted to the server (step 210) by clicking in the appropriate submit box 156. Preferably, subsequent weeks' activities can be scheduled using an 'edit next week' box 157. More sophisticated options, such as 'copy and edit last week' may be offered for convenience.

The allowable user selections 151 may be provided to any level of detail required. Although the illustrations show four basic types of activity, it will be understood that the gym activity selection could open sub-menus for specific gym programs to include different types and classes of exercise equipment, such as treadmills, rowers, bicycles, steppers, free weights and mechanical weight lifting systems. The user selections may also include organised classes, such as step classes, aerobics classes and the like. As indicated, user selection options may be dictated by the user profile, based on an earlier medical or fitness assessment of the user.

The server 10 then delivers an 'options' web page 160 (FIG. 10) by which the user may submit a selection of support options to be implemented by the system 5.

In the preferred embodiment, these options include a buddy system 161, exercise session reminders 162, kit reminders 163, benefit reminders 164 and motivational reminders 165, all as will be described below. Reminders may be delivered electronically, either by e-mail, or by text or picture message over the mobile telephony network, or even by automated voice telephone call according to the options selected from options menus 166 and 167. The destination of automated reminders may be indicated in box 168. The user selections are submitted to the server (step 210) using the submit button 169.

In a preferred arrangement, the user motivation system 5 issues automatic electronic alert messages to the user in advance of the user activity. This electronic alert message may comprise an exercise session reminder delivered a predetermined number of minutes before the time for a scheduled activity 152, 153. The number of minutes ahead of the scheduled activity time may be determined by the user to allow time to reach the activity venue. The electronic alert message may also comprise a preparation reminder delivered, for example, the evening before to remind the user to pack their kit bag for the following day's activity, if appropriate. Preferably, electronic alert messages are delivered to the user's mobile telephone 30 via the mobile telephone network 25, 26, from server 10. Preferably, the electronic alert messages comprise SMS text messages, although picture or graphics messages may also be used. Alternatively, electronic alert messages may be delivered by e-mail to the users computer system 20, or may be delivered as computer generated voice messages by telephone.

In another preferred embodiment, the user motivation system 5 includes a 'buddy' system. The user may opt to be included in the buddy system. When the buddy system is selected, the server 10 interrogates the database 40 to try to match users to support one another in exercise activities. The matching criteria used may be selected according to one or more of a number of possibilities.

These include: (i) matching personality types recorded in the user profile files 43; (ii) matching activity types, e.g. running, swimming, gym workouts etc; (iii) matching locations of activity facilities used; (iv) matching times of scheduled activities; (v) matching user's selected barriers and/or selected solutions; (vi) matching user's selected benefits; and (vii) matching physique/ability levels. The matching criteria may be required to be exact matches or close matches in respect of any or all of the applied criteria. For example, users may indicate a willingness to vary their planned schedules in order to coincide with another user who has common activities and common personality type. The buddy system may include an 'invite' web page where the user can invite specified buddies to specific activity sessions.

In another preferred embodiment, the user motivation system 5 provides a monitoring and feedback system to encourage the user to adhere to the activity schedule and to provide progress reporting. In a preferred embodiment, the feedback system includes means for confirming attendance at a scheduled activity. This could be as straightforward as the user submitting 'self-certificated' attendance confirmation by appropriate electronic dialogue with the server 10. Preferably, however, the system includes a degree of automation and independence from the user. For example, gym attendances and attendance at organised exercise classes may be confirmed by gym staff and class supervisors or instructors submitting attendance records to the server 10 by way of a suitable monitoring device 50 (FIG. 1). This monitoring device may be a suitable computer connected to the network 15 for updating the server. Attendance records may be submitted electronically and automatically by way of swipe cards and card readers or other suitable means 50 located at exercise activity locations so that electronic feedback can be provided direct from the scheduled activity location to the server 10.

Preferably, the user attendance data comprises exercise achievement data indicative of performance at specified activities. Such exercise data may be derived directly from electronically monitored physical activity devices such as treadmills, rowing machines, steppers and static bikes, for example. Exercise data may include, inter alia, exercise activity durations, distances, resistances, weights, number of repetitions etc. Preferably, each physical activity device 60, 61 is provided with a suitable means for identifying the user and is connected by suitable network to the server 10. In another arrangement, the user's mobile telephone 30 or PDA device may act as the conduit between physical activity devices 61 and the server 10, for example using a short range wireless communication link 62 between the physical activity device 61 and the mobile telephone 30, and the conventional wireless telephony network 26 between the mobile telephone and server 10.

Preferably, the attendance data is presented to the user on an 'achievement' web page 170 (FIG. 11) delivered by the server 10. The achievement web page 170 may include statistics on, for example, (i) the number of attendances per week; (ii) variances in attendances from previous weeks or from the schedule; (iii) exercise data showing performance against targets; (iv) variances in performance for individual activities, and the like.

Figure 11:
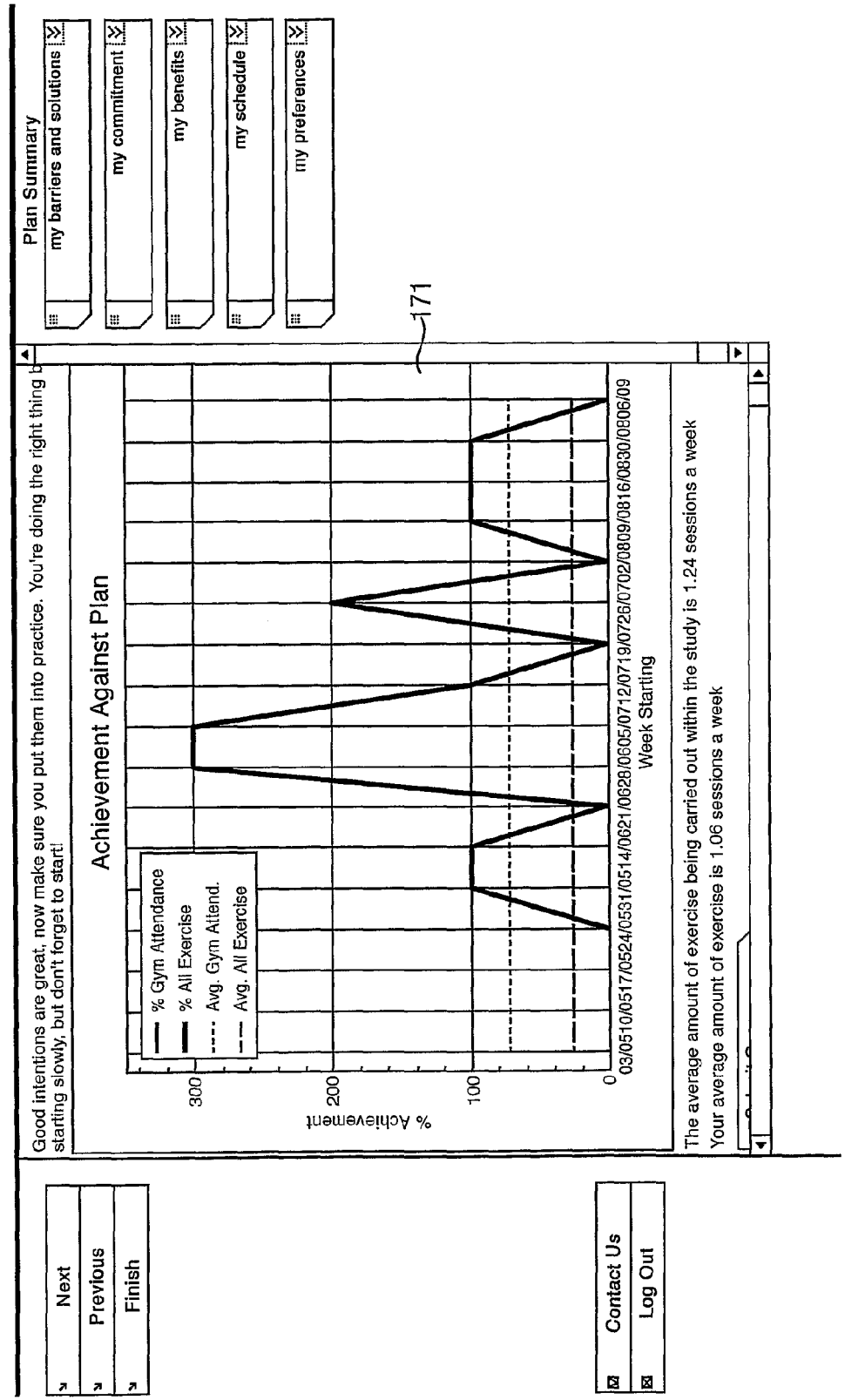
FIG. 11 is a web page, transmitted by the server of FIG. 1, displaying attendance and achievement data for a user.

The data may be displayed in graphical form 171 as shown in FIG. 11. The data for an individual's personal achievement may be supplemented with comparative data for other users of the system so that the individual may monitor personal progress against other users' progress. The comparative data may relate to all other users or only a subset of other users. For example, a suitable subset would be users having a similar profile, a similar exercise regime or a similar 'starting level' as the individual or members of a common 'buddy' group. The comparative data may be real time data (i.e. how other users are performing now) or historic data (how other users performed at a similar stage of a new exercise regime to that currently being experienced by the individual).

The user motivation system 5 may also be configured to deliver motivational messages to the user at predetermined, random or calculated intervals. The motivational messages are maintained in a file 45 in the database 40. The motivational messages may be delivered by e-mail, by text message, by picture message or by automated voice message. The motivational messages are preferably selected based on user profile, taking into account barriers and solutions selected by the user. The motivational messages may also be selected taking into account commitments and benefits selected by the user. The motivational messages may also be selected to take into account attendance performance against the user's schedule, or exercise performance against the user's targets or previous weeks' performances. The motivational messages may also be selected taking into account the user personality type as defined in the user profile 43 to determine the tone of the messages.

For example, where a user has fallen behind on attendance or exercise performance, the system 5 may, for one user personality type or characteristic, deliver encouraging messages to try to put the user back on target. Alternatively, for another user personality type, the messages may be more challenging or even 'rude' in tone. Where a user has performed ahead of target, congratulatory messages may be sent as a reward, reinforcing the good performance.

The presentation of the web pages delivered to a user computer 20 during interactions with the server 10 may be varied according to how well the user is achieving their attendance or exercise performance. For example, headings, colours and messages may change according to a user's performance.

The motivational messages delivered to a particular user may also be determined according to performance of other users of the system. For example, the messages could include average or specific performance data relating to a preselected cohort of users with whom the particular user shares some affinity, e.g. common exercise activities or classes, common weight loss program, common club membership or shared workplace and the like.

The motivational messages may also be selected from a database of tips and hints provided by other users of the system who have overcome similar hurdles or barriers to exercise with whom the specific user appears to share features in common.

The motivational messages may generally be selected according to a communication style preferred by the user, as specified in the user profile. Communication styles may encompass personality dimensions or styles, such as extravert, introvert, agreeable, argumentative, confrontational, passive etc. Communication styles may include categories such as visual, auditory or kinaesthetic sensory communication preferences. Motivation messages could be delivered in text and/or graphics form, with still and/or moving images.

Where the 'buddy' system is enabled by a user, the system 5 may alert an allocated buddy when a user falls behind in attendance or performance, so that the buddy may attempt to intervene in person and encourage the user to adhere to the schedule.

A number of other variations on the embodiments described are possible. For example, in the preferred embodiment, a commitment (steps 205, 206) is made by the user in writing, in the user's own words, (e.g. as typed text in the commitment web page 130) to enhance the user's affinity to the commitment. Other forms of input to the server 10 are possible. For example, a spoken commitment could be recorded and received which can subsequently be used for playback to the user as motivational feedback. In another arrangement, the commitment steps could involve another user or 'buddy' who may also be involved in 'witnessing' the commitment and confirming the commitment using another web page. Still further, the server 10 may provide for joint commitments established for and between multiple users of the system.

Not only the motivational messages may be adapted in communication style according to a user profile indicating user personality and information processing preferences. The communication style adaptation may also apply to solutions and for any other text based communication in the system. In another arrangement, the system may generally adapt its appearance, layout and style of interaction with the user based on information received via any of the modules within the system. The motivation system is preferably holistic in that information detected about the user via their interaction with any one of the processing modules updates the global picture of that user's profile which in turn can influence the way any of the other modules is presented or interacts with the user.

In addition to a user's personality and information processing preferences, the motivation system may also look for information on the user's state of readiness for exercise (e.g. which ranges from 'not at all interested in exercise' to 'expert exerciser') through analysis of user input and/or by asking specific questions.

As an alternative to representing users with a web page showing barriers which the user selects and then offering solutions based thereon, an automated text-based dialogue system may be used. In this arrangement, the user enters into a dialogue with the system (usually represented as a cartoon or human-like character). The system character initiates the dialogue by asking how the user is and asking what barriers they face in trying to exercise more. The user enters text which is automatically analysed by the system and matched against the set of pre-defined barriers. Once it has been confirmed that the appropriate barrier has been identified then a solution is offered, and the user is asked if this is useful/acceptable. The user may answer via text response, which again is automatically analysed to determine if the response is negative or positive. If the first solution is not acceptable then another two may be presented in series. If the solutions are still not acceptable, then the system enters into dialogue again with the user to check that the right barrier has been identified. If another barrier is then selected, a further set of solutions may be offered in the same style.

The style of dialogue and wording of the solutions may adapt during the dialogue interaction so that it more closely matches the user personality/information processing preferences. These preferences may be based on analysis of the user input.

If the system cannot find a barrier or solution that suits the user, then the dialogue may be ended and the user directed towards the web page based interaction already described above. Similarly, if the user first looks for solutions via the web page based interaction and is detected to be finding it difficult (e.g. taking a long time, repeatedly searching through the same solutions, not looking through barriers that are similar to the barrier they have been stuck in for a while, then the system may suggest they use the text based dialogue. Thus, in a general sense, the system may be adapted to switch between communication styles and means for receiving user input where interaction with the user is failing to make adequate progress towards a next stage in the process.

Other embodiments are intentionally within the scope of the accompanying claims.

The invention claimed is:

1. A system for assisting behavioural change in an individual, the system comprising:
a server configured to:
receive user input indicating at least one potential barrier to implementing a desired behavioural change;
present to the user a selected number of possible solutions to the at least one potential barrier, the possible solutions being selected from a database of solutions according to strength of association with the at least one potential barrier identified in the user input, wherein strength of association is based on popularity, among users of the system, of the possible solutions for overcoming the at least one potential barrier;
receive user input selecting at least one of said possible solutions; and
prompt the user to enter a commitment to one or more actions intended to assist the behavioural change.

2. The system of claim 1, wherein the server is further configured to:
present the user with at least one potential barrier to implementing a desired behavioural change.

3. The system of claim 1, wherein the server is further configured to:
present to the user a list of potential benefits of the desired behavioural change; and
receive user input selecting one or more of the listed potential benefits which the user considers to be motivating; and
deliver motivational messages to the user based on the selected potential benefits.

4. The system of claim 1, claim 2 or claim 3 wherein the presenting and the receiving user input comprise an automated dialogue module.

5. The system of claim 1 wherein the server is an internet server.

6. The system of claim 1 wherein the server is further configured to:
receive a user selection of exercise activities corresponding to said one or more actions, and scheduled times for the activities;
display a schedule of planned exercise activities; and
send an electronic alert message to the user in advance of a scheduled activity.

7. The system of claim 6 in which the electronic alert to be sent comprises a text or graphics message to the user's mobile telephone or computing device, the message comprising an attendance reminder for a scheduled activity.

8. The system of claim 6 in which the electronic alert to be sent comprises a text or graphics message to the user's mobile telephone or computing device, the message comprising a preparation reminder for a scheduled activity.

9. The system of claim 6, in which the electronic alert to be sent comprises a text or graphics message to the user's mobile telephone or computing device, the message comprising a motivation message to encourage attendance at the scheduled activity.

10. The system of claim 1 in which strength of association is based on a measure of efficacy for overcoming the at least one potential barrier based on multiple users of the system.

11. The system of claim 1 wherein the server is further configured to receive a said commitment from the user in written or spoken form.

12. The system of claim 11 wherein the server is further configured to analyse the user commitment for deterministic statements that can lead to measurable achievements.

13. A computer-implemented method for assisting behavioural change in an individual, the method comprising:
(a) identifying, at a server, in the individual a barrier to implementing the desired behavioural change, said barrier being selected from a predetermined list;
(b) selecting, at the server, at least one solution to the barrier using a system comprising a mapping between barriers and solutions, the selected at least one solution having highest strength of association with the barrier identified in step (a), wherein strength of association is based on popularity, among users of the system, of the at least one solution for overcoming the barrier;
(c) presenting the at least one solution to the individual;
(d) verifying the individual's acceptance of the at least one solution, with steps (b) and (c) being repeated until the individual accepts at least one solution; and
(e) prompting the individual to enter a commitment to one or more actions intended to assist the desired behavioural change.

14. The computer-implemented method of claim 13 further including the step of:
identifying from the individual at least one perceived benefit of the desired behavioural change which the individual considers to be motivating, said benefit being selected from a predetermined list.

15. The computer-implemented method of claim 14 further including the step of:
delivering motivational messages to the user based on the selected potential benefits.

16. The computer-implemented method of claim 14 wherein said barrier and said at least one perceived benefit is identified by the individual interacting with an automated dialogue module.

17. The computer-implemented method of claim 13 or claim 14 wherein the method is implemented for an individual via electronic communications.

18. The computer-implemented method of claim 13 wherein the system provides reminders for one or more of the actions in a program of actions.

19. The computer-implemented method according to claim 18 wherein the reminders are provided by electronic mail or mobile telephony.

20. The computer-implemented method according to claim 13 wherein the information provided in steps (a) and (d) is used to generate a user profile and the user profile is compared with other user profiles stored in the system to identify a profile match.

* * * * *